United States Patent [19]

Kastell

[11] Patent Number: 4,515,778
[45] Date of Patent: May 7, 1985

[54] PREPARATION FOR CONDITIONING AND GROOMING THE HAIR

[76] Inventor: Wolfgang Kastell, Milchstrasse 19, Hamburg, 13, Fed. Rep. of Germany

[21] Appl. No.: 489,066

[22] Filed: Apr. 27, 1983

Related U.S. Application Data

[63] Continuation-in-part of Ser. No. 339,419, Jan. 15, 1982, abandoned.

[30] Foreign Application Priority Data

Mar. 12, 1981 [DE] Fed. Rep. of Germany ....... 3109420

[51] Int. Cl.$^3$ ............................................. A01N 63/02
[52] U.S. Cl. ....................................... 424/95; 424/70; 424/71
[58] Field of Search .............................. 424/70, 71, 95

[56] References Cited

U.S. PATENT DOCUMENTS 4,201,235  5/1980  Ceavatta ................................ 424/47

OTHER PUBLICATIONS

Chemical Abstracts, vol. 94, (1981), Par. 71215(a), Abstract of Eur. Pat. Appl. No. 19 301, dated 26, Nov. 1980, to Spitzer et al.
Chemical Abstracts, vol. 99, (1983), Par. 10, 695(p).
Chemical Abstracts, vol. 98, (1983), Par. 22,079(h).

*Primary Examiner*—Elbert L. Roberts
*Attorney, Agent, or Firm*—Lilling & Greenspan

[57] ABSTRACT

The present invention provides a preparation for conditioning and grooming the hair. The active ingredients are vegetable lecithins, as well as cytochromes, phosphatidyl inositols, phosphatides and phosphatidic acids. Apart from the vegetable lecithins the other active ingredients are obtained by aqueous or ethereal extraction from fresh animal hearts, more particularly bovine hearts.

7 Claims, No Drawings

PREPARATION FOR CONDITIONING AND GROOMING THE HAIR

CROSS REFERENCE TO RELATED APPLICATIONS

This application is a continuation-in-part of U.S. application Ser. No. 339,419, filed Jan. 15, 1982, now abandoned.

BACKGROUND OF THE INVENTION

The present invention relates to a preparation for conditioning and grooming the hair.

BRIEF SUMMARY OF THE INVENTION

The present invention provides a preparation which conditions and grooms the hair. This preparation is simple and economical to make and easy and agreeable to use.

The excellent grooming and conditioning action of the preparation according to the invention can largely be attributed to the following findings. Sebum and dandruff deposits are removed as a result of the high proportion of phosphatides (lecithins of a vegetable and animal origin, kephalins), which are solvents for hydrophobic substances. There is in particular an in-depth action on the hair follicles. Cholesterol deposited on the cellular membranes and which blocks cellular metabolism is emulsified and transported away. This can stimulate follicle cellular metabolism.

Preferably, nutrients and build-up substances are simultaneously supplied to the follicle cells representing the growth of the hair in order to assist this process. These substances include phosphatidic acids which aid permeable membrane transport, inositols which exercise a growth function under certain conditions and cytochromes serving as catalysts on the final respiratory path. These are catalysts on the final oxidation path and bring about electron transfer between flavin enzymes and molecular oxygen. The last enzyme in the cytochrome series is cytochrome oxidase, which directly reacts with oxygen and catalyzes the oxidation of cytochrome C. By change of valency (electron valency change) copper participates in this reaction, in addition to heme iron. The activity of cytochrome oxidase is limited by lipids. According to the present invention there must be a combination of at least two of the following components in the hair preparation:
(1) Vegetable lecithins,
(2) Cytochromes, particularly cytochrome oxidase,
(3) Phosphatidyl inositols,
(4) Phosphatides, and
(5) Phosphatidic acids, particularly free phosphatidic acids.

Advantageously the preparation according to the invention contains all five substances. Although in actual fact, lecithins should be placed with the phosphatides they are indicated separately here (cf. component (1) or (4)), because components (1) and (2) to (5) are separated from one another, while taking into account the preparation process. From the chemical standpoint the most important phosphatides are kephalins and lecithins in which the base colamine or choline appears.

Advantageously component (1), i.e. vegetable lecithins are prepared by extraction from the tonic 3N lecithin of VEB Arzneimittelwerke Dresden or Buer lecithin obtained from soya beans.

Component (2), i.e. cytochromes, is the enzyme group of cellular hemins, whose biochemical function is based on the transfer of electrons, as stated hereinbefore. However, for reasons of completeness reference is made to Beyer, Lehrbuch der organischen Chemie, S. Hirzel-Verlag, Leipzig 1968, p. 743 ff.

Of particular importance for the purpose of the present invention is the process for preparing the hair conditioner and grooming agent, which is characterized by 16 different stages, as recited in claim 14, including the preparation of an animal heart, particularly a bovine or cattle heart for isolating components or active substances (2) to (5), which are then combined with component (1) in stages (15) and (16).

The hair conditioner and grooming agent according to the invention can be used in different forms, e.g., as a solution, emulsion or dispersion. The conditioner and grooming agent should be applied substantially externally, but internal application is not excluded. It is known that in the case of epicutaneous application, the preparations remain on the scalp after application. These consist of hair lotions or tonics which, as is known, have as their main constituents water, ethanol or isopropanol. However it is also possible to use ointments, gels, creams emulsions and in particular, suspensions. The hair preparation according to the invention is advantageously stored so that it is protected from light and kept at low temperature. At this point reference is also made to the subclaims, which give further advantages and features, which can all be of significance for the present invention.

The preparations according to the present invention may also contain conventional cosmetic substances for caring for the hair and scalp, as well as further known medically active ingredients. Particular reference is made to anti-dandruff and anti-seborrheic products, as well as vitamins, hormones, preservatives and other similar substances, which must obviously be compatible with the constituents according the invention and must not prevent growth of the hair.

Obviously the scalp should be pretreated together with the hair or cleaned with conventional products, so that as far as possible no fatty substances prevent the penetration of the hair conditioner and grooming agent according to the invention.

DESCRIPTION OF PREFERRED EMBODIMENTS

The invention is described in greater detail hereinafter relative to a number of non-limitative exemplified embodiments.

EXAMPLE I

Alcoholic hair lotion in the form of a suspension (approximately 1 liter):
400 mm. of absolute ethanol
400 ml. of distilled water
50 g. of vegetable lecithins
Cytochromes, phosphatidyl inositols
Free phosphatidic acids
Lecithins as an extract from 250 g. of fresh bovine heart.

EXAMPLE II (Preparation Process)

Fatty residues are removed with a sharp knife from 250 g. of fresh bovine heart, which is minced in a mincer-like scraped meat, giving a homogeneous paste which is fed into a 1 liter beaker. This is then topped up to 0.5 liters with distilled water and the paste is then stirred for about 30 minutes with a mixer on the lowest stage.

The aqueous slurry or paste is then placed on a soft folded filter and the aqueous filtrate collected. The meat residues are stored.

The resulting filtrate is briefly boiled, i.e. heated to boiling. However, as soon as a fine precipitate is formed, it is immediately stopped and filtration again takes place. The precipitate is discarded, and the aqueous solution obtained can be termed a cytochrome solution, which is stored for further processing at a refrigerator temperature of 6° C.

The meat residues separated after the first filtration are added to approximately 250 ml. of absolute of ether and stored for two days at ambient temperature in an air-tight, sealed dark vessel with a screw cap. It must be ensured that there is no escape of the ether.

The resulting ethereal solution is then filtered and separated from the meat residues, which are then discarded. The solution is transferred into a 1 liter separating funnel, where the aqueous, reddish solution is separated from the supernatant ethereal, yellowish solution. The aqueous red solution is discarded. During phase separation the separating funnel is left to stand for a short time to improve the phase separation. The ether is then removed at normal pressure using an electrically heated waterbath and the residue is then immediately suspended in the distilling flask with 2×75 ml. of distilled water. It is assumed that this suspension essentially contains phosphatidyl inositols, free phosphatidic acids and lecithins.

This suspension is then combined with the stored aqueous cytochrome solution and then 50 g. of vegetable lecithin are added, which have been extracted from the tonic 3N lecithin (VEB Arzneimittelwerke Dresden). 400 ml. of absolute ethanol are then added to the resulting suspension and the latter may optionally be topped up to 1 liter with distilled water.

EXAMPLE III 100 ml. contain:

| | |
|---|---|
| ethanol | 35.0 |
| lecithin | 5.0 |
| L-cystin | 0.0001 |
| ascorbinic acid | 0.0001 |
| deionized water ad | 100.0 |

The water contains the watery extract as well as the residue suspended in water and prepared from the ether fraction.

EXAMPLE IV

Fatty residues are essentially removed from 250 g. of bovine heart, which is minced in a mincer. 300 ml. of 0.02 m phosphate buffer, pH=7.2, containing 0.1% sodium azide are added and the mixture is stirred in a mixer for 2 to 3 minutes. This mixture is sucked and pressed through a moistened filter having wide pores, and is separated by a high speed centrifuge. The resulting filtrate or the output of the centrifuge respectively is briefly boiled; after cooling down the denatured proteins are separated by a folded filter and discarded. The filtrate (I) containing the cytochromes is stored in the refrigerator until further processing. The remaining meat residues are briefly pressed between filter paper, 300 ml. i-dropanol is poured on them, a drop of tocopherol is added, and the mixture is stirred for 20 minutes. Thereafter the mixture is passed through a Buechner filter and evaporated essentially to dryness in a rotating evaporator. The still moist residue is resuspended with about 100 ml. water and 50 ml. ethanol (Suspension II). The vegetable lecithin (50 g.) is suspended in 500 ml distilled water, stirring vigorously. To this are added, one after the other, the filtrate I and the suspension II, while the mixture is stirred vigorously. Then 350 ml. ethanol are added in a thin stream under stirring and the mixture is topped up to 1000 ml with distilled water.

What is claimed is:

1. A process for preparing a hair conditioner, comprising the following steps:
    (1) cleaning a bovine heart, including removing fatty residues;
    (2) mincing the cleaned heart, to form a pasty mixture;
    (3) adding distilled water in approximately the same quantity as the heart;
    (4) stirring the pasty mixture and allowing it to stand for approximately 24 hours in a sealed vessel at approximately 4° C.;
    (5) filtering the mixture, and separating it into
        (a) a filtrate, and
        (b) meat residues;
    (6) briefly heating the filtrate to boiling until a fine precipitate forms;
    (7) filtering the fine precipitate formed in step (6) and recovering the filtrate;
    (8) adding approximately the same quantity of ether to the meat residue separated in step (5) (b);
    (9) storing the mixture prepared in step (8) for several hours in a sealed vessel at ambient temperature;
    (10) filtering the ethereal mixture obtained in step (9), and separating into (a) filtrate and (b) meat residues;
    (11) separating the ethereal phase from the filtrate obtained in step (10) (a);
    (12) distilling the ether from the ethereal phase obtained in step (11), to obtain a residue;
    (13) suspending in water the residue comprising phosphatidyl inositol, phosphatide and phosphatidic acid;
    (14) combining the aqueous suspensions or solutions prepared in steps (7) and (13);
    (15) adding vegetable lecithin in approximately 2 to 15% by weight to the suspension of step (14);
    (16) adding absolute ethanol in approximately the same weight as the suspension of step (15).

2. The process of claim 1, step (7) wherein the filtrate is stored at 4° to 10° C. until further use.

3. The process of claim 1, step (9), wherein the mixture is stored for several days.

4. The process of claim 3, wherein the mixture is stored for two days.

5. The process of claim 1, step (15), wherein the amount of vegetable lecithin is approximately 5 to 10% by weight.

6. The process of claim 1, step (16), wherein water is also added.

7. The process of claim 1, wherein the vegetable lecithins added in step (15) are obtained from soya beans.

* * * * *